United States Patent
Boebel et al.

(10) Patent No.: US 9,662,141 B2
(45) Date of Patent: May 30, 2017

(54) COLPOTRANSILLUMINATOR FOR ARRANGEMENT IN A UTERUS MANIPULATOR

(71) Applicant: Richard Wolf GmbH, Knittlingen (DE)

(72) Inventors: Manfred Boebel, Bauschlott (DE); Eberhard Körner, Knittlingen (DE); Reiner Klostermann, Bretten (DE)

(73) Assignee: Richard Wolf GmbH, Knittlingen (DE)

( * ) Notice: Subject to any disclaimer, the term of this patent is extended or adjusted under 35 U.S.C. 154(b) by 329 days.

(21) Appl. No.: 14/224,356

(22) Filed: Mar. 25, 2014

(65) Prior Publication Data
US 2014/0303641 A1    Oct. 9, 2014

(30) Foreign Application Priority Data
Mar. 25, 2013    (DE) .................. 10 2013 205 201

(51) Int. Cl.
| A61B 17/42 | (2006.01) |
| A61B 90/30 | (2016.01) |
| A61B 17/00 | (2006.01) |
| A61B 17/30 | (2006.01) |

(52) U.S. Cl.
CPC .......... A61B 17/4241 (2013.01); A61B 90/30 (2016.02); *A61B 2017/00473* (2013.01); *A61B 2017/00862* (2013.01); *A61B 2017/00902* (2013.01); *A61B 2017/308* (2013.01); *A61B 2090/306* (2016.02); *A61B 2090/309* (2016.02)

(58) Field of Classification Search
CPC ............... A61B 17/4241; A61B 90/30; A61B 2017/00473; A61B 2017/00862;
(Continued)

(56) References Cited

U.S. PATENT DOCUMENTS 5,209,754 A    5/1993    Ahluwalia
6,516,216 B1    2/2003    Fontenot et al.
(Continued)

FOREIGN PATENT DOCUMENTS

| DE | 10 2009 056 705 A1 | 6/2011 |
| EP | 1759645 A1 | 3/2007 |
| WO | 2010/151429 A2 | 12/2010 |
| WO | 2010141423 A1 | 12/2010 |
| WO | 2011140604 A1 | 11/2011 |

OTHER PUBLICATIONS

Extended European Search Report issued Jun. 30, 2014 in EP Application No. 14161089.9.
(Continued)

*Primary Examiner* — Eric Rosen
*Assistant Examiner* — George J Ulsh
(74) *Attorney, Agent, or Firm* — Panitch Schwarze Belisario & Nadel LLP

(57) ABSTRACT

A colpotransilluminator is provided for arrangement on a uterus manipulator, wherein the colpotransilluminator is designed in a sleeve-shaped manner of an elastic material. The colpotransilluminator at a distal first axial end forms a portio receiver and at a proximal second end forms a vaginal seal. In a central region between the first and the second axial ends, the colpotransilluminator is designed in a waist-shaped manner and includes axially extending stretch folds in the region of the waist. A uterus manipulator is also provided with such a colpotransilluminator.

17 Claims, 4 Drawing Sheets

(58) Field of Classification Search
CPC .... A61B 2017/00902; A61B 2090/309; A61B 2090/306; A61B 17/42; A61B 2017/308; A61B 2017/4216; A61B 2017/4225; A61B 17/0057; A61B 2017/00592; A61B 17/3423; A61M 39/0247; A61M 29/00; A61M 2029/025
USPC ...... 606/119, 120–126, 213; 604/30, 35, 27, 604/158, 264
See application file for complete search history.

(56) References Cited

U.S. PATENT DOCUMENTS

| | | | |
|---|---|---|---|
| 6,641,604 B1 * | 11/2003 | Adelman | A61B 17/02 600/37 |
| 8,568,423 B2 | 10/2013 | Boebel et al. | |
| 2011/0130769 A1 * | 6/2011 | Boebel | A61B 17/4241 606/119 |
| 2012/0330324 A1 | 12/2012 | Sauer | |
| 2013/0190571 A1 * | 7/2013 | Chen | A61B 17/3423 600/204 |

OTHER PUBLICATIONS

German Search Report issued on Nov. 26, 2013 in German Application No. 10 2013 205 201.4.

* cited by examiner

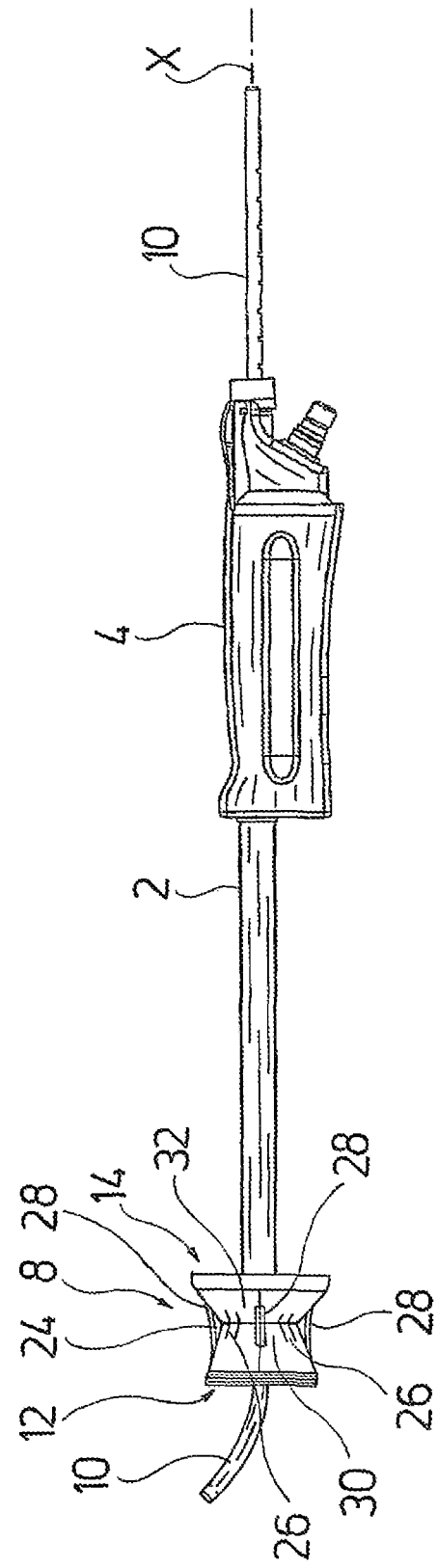

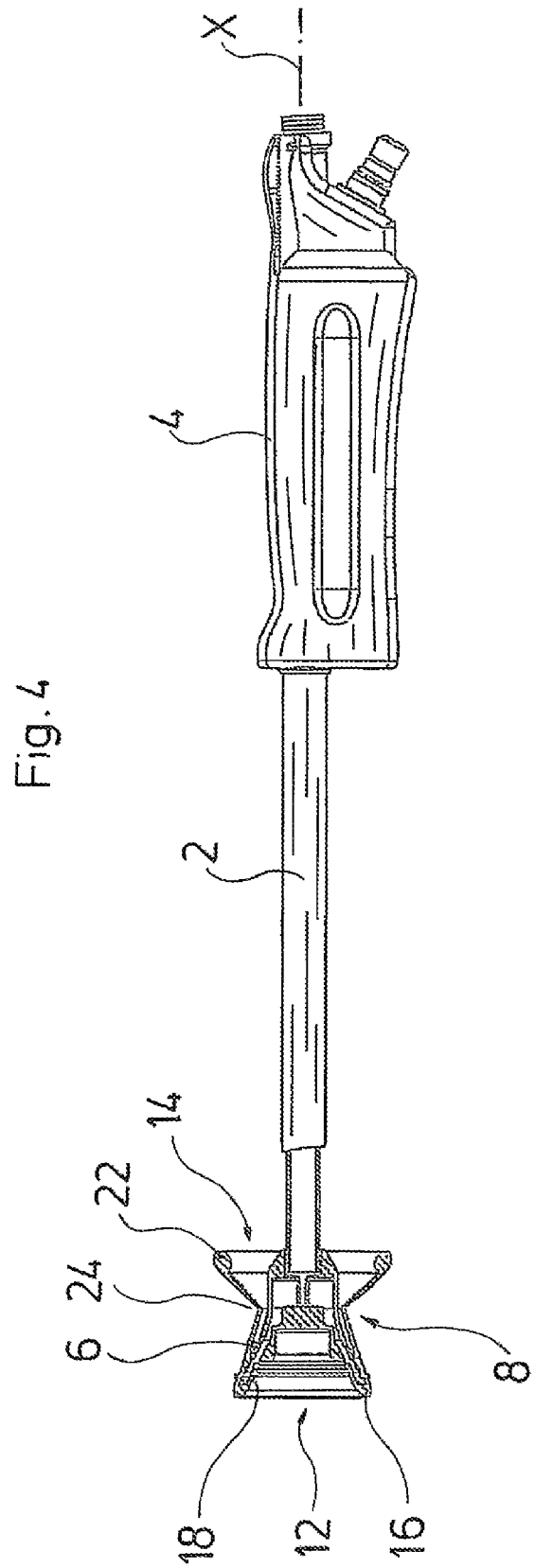

COLPOTRANSILLUMINATOR FOR ARRANGEMENT IN A UTERUS MANIPULATOR

BACKGROUND OF THE INVENTION

The invention relates to a colpotransilluminator for arrangement on a uterus manipulator, as well as to such a uterus manipulator.

A uterus manipulator is known from German published patent application DE 10 2009 056 705 A1, which at its distal end comprises a removable double bell, whose distal end forms a portio receiver and whose proximal end forms a vaginal seal. Such an instrument is used for laparoscopically assisted vaginal hysterectomy and serves for holding and leading the uterus through the vagina from the outside. The bell arranged at the distal end of the instrument thereby serves for receiving the portio, for the illumination of the rear vaginal fornix as well as for the gas-tight closure of the vagina and, optionally, additionally for insulation with the use of HF-instruments. The bell thereby should be designed in a removable manner and must be suitable for use with different anatomical conditions.

BRIEF SUMMARY OF THE INVENTION

It is the object of the invention, to provide a removable colpotransilluminator which is envisaged for arrangement on a uterus manipulator and ensures an improved adaptation to different anatomical conditions, and a simple removability from the uterus manipulator.

This object is achieved by a colpotransilluminator designed in a sleeve-shaped manner and made of an elastic material, which at a first distal axial end forms a portio receiver and at a second proximal axial end forms a vaginal seal. The colpotransilluminator is designed in a waist-shaped manner in a central region between the first and the second axial end, and comprises axially extending stretch folds in the region of the waist.

The object is further achieved by a uterus manipulator, in particular for laparoscopically assisted vaginal hysterectomy, having a shank on which a distal end section and a proximal handle are arranged, wherein a colpotransilluminator according to the above is releasably applied on the distal end section.

Preferred embodiments may be deduced from the dependent claims, the subsequent description, as well as the attached figures.

The colpotransilluminator according to the invention is envisaged and designed for arrangement on a uterus manipulator. Thereby, the colpotransilluminator forms that component at the distal end of the shank of the uterus manipulator, which serves for receiving the portio and for sealing the vagina to the outside. The colpotransilluminator thus represents the removable receiving and sealing bell at the distal end of a uterus manipulator.

According to the invention, the colpotransilluminator is designed as an elastic tubular sleeve which can be put or pulled onto the distal end of a uterus manipulator. Thereby, in the direction of the longitudinal axis of the sleeve, which corresponds to the longitudinal axis of the uterus manipulator, a first distal axial end of the sleeve forms a portio receiver which, with the use of the uterus manipulator, serves for receiving and fixing the portio, i.e. the portio vaginalis uteri. The opposite, second proximal axial end of the sleeve-shaped colpotransilluminator forms a vaginal seal. That is, this section of the sleeve comes to sealingly bear on the inner wall of the vagina and thus seals this to the outside, so that with the laparoscopic severing of the rear vaginal fornix, the pneumoteritoneum prevailing in the abdominal cavity does not collapse due to gas escaping via the vagina.

According to the invention, the sleeve of the colpotransilluminator is formed of an elastic material. This has the advantage that a certain elastic deformation is possible, so that an adaptation to different anatomical conditions is possible. The sleeve of the colpotransilluminator is designed in a waist-shaped manner in a central region between the first and the second axial ends. That is, the central region in the idle condition of the sleeve has a smaller diameter than the two axial ends. Axially extending stretch folds are formed in the region of this waist. These stretch folds have walls which extend transversely to the peripheral direction of the sleeve and permit the wall in the central region to stretch in the peripheral direction, so that a radial widening of the inner diameter is possible due to a stretching of the folds in the peripheral direction. This permits the colpotransilluminator to be pulled over a receiver, widened in diameter, at the distal end of the uterus manipulator, and thus permits the colpotransilluminator to be fixed at the distal end of the uterus manipulator.

The uterus manipulator at its distal end preferably comprises a conical or essentially truncated-cone-shaped receiver, wherein the larger outer diameter of the receiver is situated at the distal end, and the smaller diameter is situated further proximally. The colpotransilluminator can be pulled from the distal end over such a receiver, so that the smallest diameter of the colpotransilluminator in the central region is situated on the proximal side of the largest diameter of the receiver. Thus, the first axial end of the colpotransilluminator, which forms the portio receiver, then lies distally of the receiver at the distal end of the uterus manipulator, and the vaginal seal lies on the proximal side. The portio receiver as well as the vaginal seal are moreover preferably designed in an essentially bell shaped manner by the waist.

Preferably, several stretch folds are arranged or formed in a manner distributed over the periphery of the central region. Thereby, the stretch folds are further preferably uniformly distributed over the periphery. Particularly preferably, the complete periphery is provided with stretch folds, so that the central region, seen in cross section normal to the longitudinal axis, comprises a zigzag or fold structure of the sleeve which runs over the entire periphery. The walls of the folds thereby seen in cross section stretch in a zigzag manner with respect to the peripheral direction, i.e., transversely or at an acute angle to the peripheral direction. The folds are pulled apart in the peripheral direction for widening the central region, so that the angle of the walls of the folds to one another increases.

According to a particularly preferred embodiment, additionally to the described stretch folds, at least one axially extending reinforcement web is arranged in the central region. The at least one reinforcement web serves for preventing the second proximal axial end forming the vaginal seal from being folded over in the distal direction, or for rendering this more difficult. The walls of the folds extending transversely in the peripheral direction also lead to a reinforcing effect, which additionally prevents the folding-over. Preferably, several reinforcement webs are arranged in a manner distributed over the periphery.

In particular, several reinforcing webs uniformly distributed over the periphery are provided, for example four reinforcement webs which are arranged at an angle of 90° to one another in each case. The at least one or the several reinforcement webs are preferably arranged on the outer periphery of the central region. Preferably thereby, the reinforcement webs intersect, or the at least one reinforcement web intersects the waist in a sinew-like manner, i.e., the reinforcement web forms a wall which extends transversely to the periphery and which connects the two conical outer surfaces of the waist, which face one another, in a sinew-like manner.

The at least one reinforcement web thereby preferably projects in the radial direction from the outer periphery of the central region. The inner periphery of the central region is advantageously not influenced by the reinforcement web or webs, so that the inner periphery of the central region can come to bear on a receiver of the uterus manipulator preferably in a fully peripheral manner.

Further preferably, the at least one reinforcement web extends in the axial direction parallel to the stretch folds, which likewise extend in the axial direction from the proximal end to the distal end, i.e., parallel to the instrument longitudinal axis. Thus, an optimal reinforcement preventing a folding-over of the second axial end of the sleeve is achieved.

Further preferably, the colpotransilluminator has a circular cross section at least in the region of one axial end, preferably at least in the region of both axial ends. Thereby, the sleeve which forms the colpotransilluminator, in its idle position (i.e., without elastic deformation), has the corresponding circular cross section, and the shape can change by way of elastic deformation. Particularly preferably, the colpotransilluminator over its entire axial length has a cross section of a circular basic shape. That is, the stretch folds are arranged in a manner distributed along a circular peripheral line, in the central region, in which they are arranged.

According to a further preferred embodiment, the diameters of the two axial ends of the colpotransilluminator are designed differently large, wherein preferably the second axial end forming the vaginal seal has a larger diameter than the first axial end forming the portio receiver. The diameter, in the intermediately lying waist-shaped central region, in particular the outer diameter is thereby preferably designed smaller than the outer diameter at the first axial end, which forms the portio receiver. A more reliable sealing on the inner wall of the vagina is achieved due to the greater design of the diameter of the vaginal seal.

The colpotransilluminator further preferably comprises a bead-like ring, at least at one axial end, preferably at both axial ends. That is, the sleeve is preferably designed in a thickened manner at the axial ends. This thickened, bead-like ring gives the axial end a certain shape stability, which contributes to the component in its idle position moving into this preferably circular basic shape.

According to a further preferred embodiment, the colpotransilluminator at its first axial end forming the portio receiver comprises an inwardly directed collar, which is designed for gripping around a distal end section of the uterus manipulator. Thus, the first axial end of the colpotransilluminator can form the distal front face edge of the uterus manipulator. Thus, the collar at the distal end of the uterus manipulator, when the colpotransilluminator is placed on this, forms an elastic inner wall for the portio receiver, which leads to a good and sealed bearing contact on the tissue.

The collar extends preferably at least in parts proximally in the axial direction. That is, it is not or not only directed radially inward at the distal end of the colpotransilluminator, but preferably extends at an acute angle to the instrument longitudinal axis or the longitudinal axis of the colpotransilluminator or parallel to the longitudinal axis in the direction of the proximal end. The collar can thus encompass a bell-shaped receiver at the distal end of the uterus manipulator on the inner periphery. The colpotransilluminator thereby extends around the distal face edge of this bell-shaped receiver and then over its outer periphery further proximally to its second proximal end. Thus the distal face edge of the uterus manipulator is completely enclosed by the colpotransilluminator, which serves for the secure receiving of the portio receiver, an improved illumination and electrical insulation with the use of HF instruments.

In order to be able to assume the desired illumination function, the colpotransilluminator is advantageously manufactured of a transparent material, at least at its first axial end and preferably completely. Illumination elements, such as light diodes or the ends of fiber optics for example, are arranged in the uterus manipulator at the distal end. The light which is emitted by these can penetrate the transparent material of the colpotransilluminator at its distal first axial end, wherein the first axial end of the colpotransilluminator is preferably thereby designed such that it ensures a light distribution and beaming preferably in the distal direction. This can be effected for example via a bead-like thickening at the distal end. The thus irradiated light with the operation serves for illuminating the rear vaginal fornix. Preferably, the complete colpotransilluminator is manufactured of transparent material. This particularly results when the colpotransilluminator, as is further preferred, is manufactured as one piece of a plastic material, such as a silicone.

According to a further preferred design, the central region with the stretch folds is designed in a manner such that the central region in the region of its smallest diameter by way of the stretch folds can elastically stretch to at least a diameter which corresponds to the inner diameter at the first end, i.e. the distal axial end. This design permits a uterus manipulator, with its receiver formed at the distal end, to be introduced into the colpotransilluminator from the second proximal end, wherein the receiver then amid the widening of the central region can pass this region and come to bear on the inner periphery of the colpotransilluminator, in the region of the distal end of this colpotransilluminator. Thereby, the distal end of the receiver of the uterus manipulator preferably is encompassed by a collar at the distal end of the colpotransilluminator, as previously described. The uterus manipulator preferably comprises a rigid receiver for the colpotransilluminator. Despite this, it is possible for this rigid receiver to be led through the narrowed or waist-shaped central region amid the elastic widening of this, due to the stretching ability on account of the stretch folds in the central region.

The subject matter of the invention is moreover a uterus manipulator, in particular for a laparoscopically assisted vaginal hysterectomy, which comprises a shank, on which a distal end section is arranged, and on which a handle situated at the proximal end is arranged. The distal end section forms a receiver, onto which a colpotransilluminator according to the preceding description is applied in a releasable manner. The colpotransilluminator represents a receiving or sealing bell. The colpotransilluminator thereby with its distal end forms a portio receiver and with its proximal end a vaginal seal, as has been described beforehand. Preferably, the uterus manipulator at its distal end section, which forms the receiver for the colpotransilluminator, has a radial widening onto which the colpotransilluminator is applied in a releasable manner. In particular, the distal end of the uterus manipulator is essentially designed in a bell-shaped manner, wherein the end section forming the receiver widens radially to the distal end, so that it has an essentially conical or truncated-cone-shaped outer contour, on which the colpotransilluminator bears with its inner contour situated on the distal side of the narrowest section. Thereby, due to the waist of the colpotransilluminator, it is possible for this to bear with its inner peripheral surface on the conical or truncated-cone-shaped region of the receiver of the uterus manipulator. Thereby, the stretch folds with their radially inwardly situated sections come to bear on this outer peripheral surface of the uterus manipulator, in the central region of the colpotransilluminator.

That is, preferably, the uterus manipulator in its distal end section is designed such that it tapers in the proximal direction from a widening at the distal end section, wherein this tapering in its shape has an essentially conical outer contour which is adapted to the conical inner contour of the distal side of the waist-shaped central region of the colpotransilluminator, in a manner such that this central region with its inner periphery can come into bearing contact on the tapering of the uterus manipulator. The previous description of the colpotransilluminator, in whose context the essential aspects of the uterus manipulator have already been described, is referred to with regard to the further design of the uterus manipulator.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a schematic longitudinal lateral view of a uterus manipulator with the colpotransilluminator according to an embodiment of the invention;

FIG. 4 is a sectioned view of the instrument according to FIG. 1; and

DETAILED DESCRIPTION OF THE INVENTION

Figure 5:
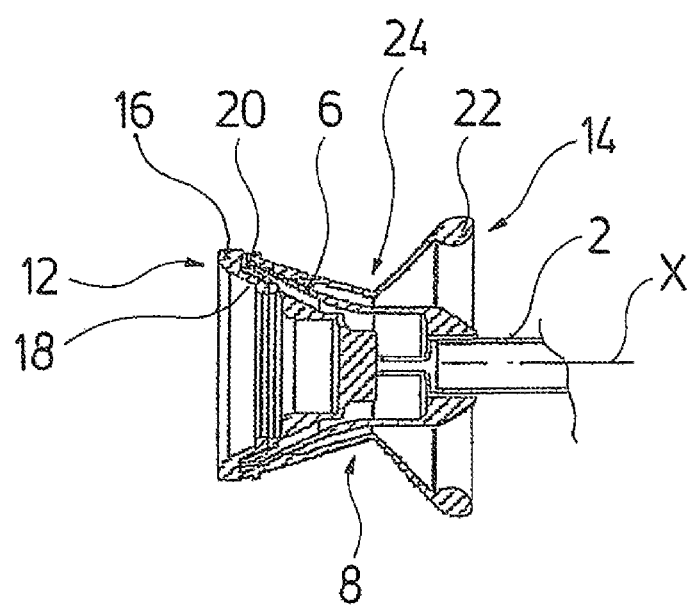
FIG. 5 is an enlarged view of the distal end of the uterus manipulator according to FIG. 4.

The uterus manipulator according to the invention comprises a shank 2, on whose proximal end a handle 4 and at whose distal end a distal end section are formed, the distal end section being designed as a receiver 6 (see FIGS. 4 and 5) for the colpotransilluminator 8. This represents a receiving and sealing bell and is placed onto the receiver 6. A hollow probe 10 which exits at the distal end of the shank 2 out of the colpotransilluminator 8 and projects in the distal direction is led through the inside of the shank 2. The hollow probe 10 is displaceable in the shank 2 in the axial direction X in defined locking steps.

The colpotransilluminator 8 at its first distal axial end 12 forms a portio receiver and at its opposite second proximal axial end 14 forms a vaginal seal. The colpotransilluminator 8 is formed from an elastic transparent material, in particular of an elastic plastic or elastomer, such as silicone.

At its first axial end 12, the sleeve-shaped colpotransilluminator 8 comprises an annular shaped peripheral bead 16. A collar 18 projecting inwardly and to the proximal end in the direction of the longitudinal axis X extends in a manner departing from this bead. The collar 18 extends proximally over the complete inner periphery of the distal end 12 of the colpotransilluminator 8 at an acute angle to the longitudinal axis X. The collar 18 thus encompasses the distal end of the receiver 6 at the distal end of the shank 2 of the uterus manipulator. The receiver 6 at its distal end is radially widened, i.e. has its greatest diameter there, and tapers in the proximal direction, so that as a whole a conical or truncated-cone shape is formed on the outer periphery. A similar contour is given at the inner periphery, so that the distal end of the receiver 6 is designed in a bell-shaped manner. The collar 18 engages over the distal annular edge 20 of the receiver 6, so that the bead 16 is situated at the axial side of the edge 20. The receiver 6 with the pushed-over collar 18 forms the portio receiver, with which the portio is fixed with the operation. Light exit openings of fiber optics (not shown here) or illumination elements, such as light diodes, are arranged in the region of the edge 20, and these couple their emitted light into the bead 16, so that the light beams out of these outwardly, in particular in the distal direction and thus illuminate the rear vaginal fornix during the operation.

The colpotransilluminator 8 at its second proximal axial end 14 comprises an annular bead 22 which has the shape of an annulus, but is elastically deformable. The bead 22 on account of its elastic restoring forces ensures that the second axial end 14 is kept in this shape in its idle condition. The second proximal axial end 14 with the bead 22 forms a vaginal seal which can come into sealing bearing contact on the inner wall of the vagina. The sleeve-shaped colpotransilluminator as a whole and also in the region of the bead 22 is elastically deformable, in order here to be able to adapt to the given anatomical shape. Thereby, it is held in sealing bearing contact with the inner wall of the vagina by way of the elastic restoring forces. The proximal end of the colpotransilluminator 8 thus likewise forms a bell which is open to the proximal end, i.e. opposite to the bell which is formed by the first axial end 12 and which forms the portio receiver.

The sleeve-shaped colpotransilluminator is designed in a waist-shaped manner in a central region between the first distal axial end 12 and the second proximal axial end 14. That is, here there is a radially inwardly directed necking 24. The necking 24 defines the smallest diameter of the colpotransilluminator. The colpotransilluminator 8 has its greatest outer diameter at its second axial end 14, which forms the vaginal seal. The colpotransilluminator at the first axial end 12, which forms the portio receiver, has an outer diameter which is greater than the outer diameter in the region of the necking 24, and in this example however is smaller than the outer diameter of the bead 22 at the second axial end 14. The inner diameter in the region of the necking 24 in the relaxed condition of the material of the colpotransilluminator is smaller than the outer diameter of the edge 20 of the receiver 6 of the uterus manipulator. It is necessary to introduce the receiver 6 with the edge 20 in front into the second axial end 14 of the colpotransilluminator 8, in order to be able to pull the colpotransilluminator 8 from the distal end over the receiver 6. Subsequently, the necking 24 must be widened in the peripheral or radial direction, so that the edge 20 of the receiver 6 can pass the necking 24.

Figure 3:
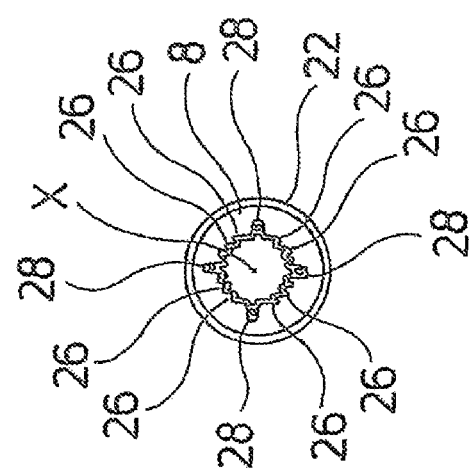
FIG. 3 is a face-side plan view of the colpotransilluminator according to FIG. 2.
Figure 2:
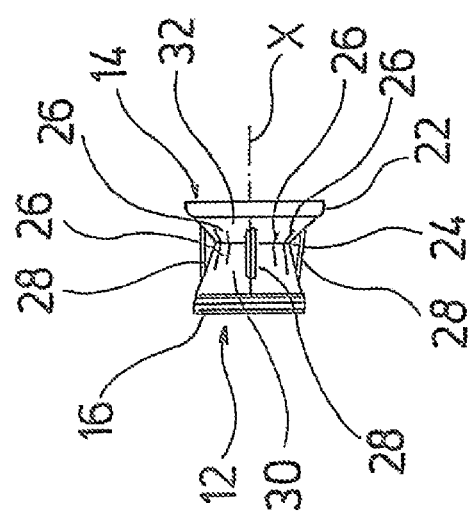
FIG. 2 a lateral view of the colpotransilluminator according to FIG. 1.

According to the invention, this is favored by the arrangement of stretch folds 26. The stretch folds 26 are arranged in the central region in the region of the necking 24 and extend to the longitudinal axis X. As can be recognized in FIG. 3, the stretch folds 26, in a cross section transverse to the longitudinal axis X, form a zigzag course of the wall of the colpotransilluminator 8. The stretch folds 26 permit a great stretching in the peripheral direction, so that the edge 20 of the receiver 6 can pass the necking 24 without any problem, amid the elastic widening of the colpotransilluminator 8. The distal-side region of the waist, i.e. the conical or truncated-cone-shaped section of the colpotransilluminator 8, which is situated distally of the necking 24, bears on the outer side or on the outer periphery of the receiver 6, when the colpotransilluminator 8 bears on the receiver 6. In this region, the inner edges of the stretch folds 26, which define a distal conical surface 30, then bear on the outer surface of the receiver 6. Thus, a firm bearing contact of the colpotransilluminator 8 on the receiver 6 is ensured. Moreover, an as small as possible outer diameter is created in the region of the necking 24, so that the space which the instrument takes up in the vagina is minimized, and thus an adequate amount of free space is left for the operation.

Moreover, reinforcement webs 28 are formed on the colpotransilluminator shown here, in order to prevent a folding-over of the proximal section of the colpotransilluminator 8 and of the bead 22, given a movement of the uterus manipulator with the colpotransilluminator 8 in the proximal direction in the vagina. The reinforcement webs 28 extend outward in a ribbed manner in the radial direction, on the outer periphery of the colpotransilluminator 8. Thereby, the reinforcement webs 28 extend parallel to the stretch folds 26 and to the instrument longitudinal axis X. The reinforcement webs 28 in the region of the waist extend such that they extend in a sinew-like manner past the necking 24 and thus connect the distal conical surface 30 to the proximal conical surface 32 adjacent to the necking 24. In the example shown here, four reinforcement webs 28 are provided, which are arranged in each case at an angle of 90° to one another. Stretch folds 26 are arranged directly adjacent to the reinforcement webs 28, so that the reinforcement webs 28 essentially do not compromise the stretching ability in the region of the necking 24, i.e. in the central region of the sleeve-shaped colpotransilluminator 8. The reinforcement webs 28 in particular support the proximal conical surface 32 or conical outer contour which connects the necking 24 to the bead 22 at the second axial end 14, so that this proximal conical surface 32 is secured against an unintended folding-over in the distal direction. Thus, a folding over of the vaginal seal is prevented when retracting the colpotransilluminator in the vagina in the proximal direction.

The complete colpotransilluminator 8 in this example is formed as one piece of plastic, in particular of elastomer or silicone, and in a transparent manner, in order to effect a light-transmitting function in the region of the distal axial end 12.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A colpotransilluminator for arrangement on a uterus manipulator, the colpotransilluminator comprising a sleeve-shaped elastic material having a distal axial end forming a portio receiver and a proximal axial end forming a vagina seal, the proximal and distal axial ends defining a longitudinal axis extending therebetween, and a central region extending along the longitudinal axis between the proximal and distal axial ends, the central region defining a radially inward necking relative to the proximal and distal axial ends in a direction perpendicular to the longitudinal axis and comprises stretch folds extending along the longitudinal axis solely in the central region.

2. The colpotransilluminator according to claim 1, further comprising at least one axially extending reinforcement web arranged in the central region.

3. The colpotransilluminator according to claim 2, wherein the at least one reinforcement web is arranged on an outer periphery of the central region.

4. The colpotransilluminator according to claim 2, wherein the at least one reinforcement web projects in a radial direction from an outer periphery of the central region.

5. The colpotransilluminator according to claim 2, wherein the at least one reinforcement web extends axially parallel to the stretch folds.

6. The colpotransilluminator according to claim 1, wherein the sleeve-shaped elastic material has a circular cross section at least in a region of one of the proximal and distal axial ends.

7. The colpotransilluminator according to claim 1, wherein the proximal and distal axial ends have different diameters.

8. The colpotransilluminator according to claim 7, wherein the proximal axial end forming the vaginal seal has a greater diameter than the distal axial end forming the portio receiver.

9. The colpotransilluminator according to claim 1, further comprising a bead-shaped ring at least at one of the proximal and distal axial ends.

10. The colpotransilluminator according to claim 1, wherein the distal axial end forming the portio receiver comprises an inwardly directed collar designed for encompassing a distal end section of a uterus manipulator.

11. The colpotransilluminator according to claim 10, wherein the collar at least partially extends in an axial direction to the proximal axial end.

12. The colpotransilluminator according to claim 1, wherein the colpotransilluminator comprises a transparent material at least at the distal axial end.

13. The colpotransilluminator according to claim 1, wherein the central region is designed such that in a region of its smallest diameter, by way of the stretch folds, the central region can stretch elastically to at least a diameter corresponding to an inner diameter of the distal axial end.

14. A uterus manipulator comprising a shank having a distal end section, a proximal handle, and a colpotransilluminator according to claim 1 releasably applied on the distal end section.

15. The uterus manipulator according to claim 14, wherein the distal end section comprises a radial widening on which the colpotransilluminator is releasably applied.

16. The uterus manipulator according to claim 14, which is designed for laparoscopically assisted vaginal hysterectomy.

17. A uterus manipulator comprising:
a shank comprising a distal end section having a radial widening and a proximal handle; and
a colpotransilluminator comprising a sleeve-shaped elastic material having a distal axial end forming a portio receiver, a proximal axial end forming a vagina seal and a central region extending between the proximal and distal axial ends, wherein the central region has a waist shape and comprises axially extending stretch folds in a region of the waist shape;

wherein the colpotransilluminator is releasably applied on the radial widening of the distal end section of the shank, and wherein departing from the radial widening at the distal end section, the uterus manipulator tapers in a proximal direction, the taper being adapted in its shape to a conical inner contour of a distal side of the waist-shaped central region of the colpotransilluminator, such that an inner periphery of the colpotransilluminator bears on the taper.

* * * * *